United States Patent
Rather et al.

(10) Patent No.: US 6,672,165 B2
(45) Date of Patent: Jan. 6, 2004

(54) REAL-TIME THREE DIMENSIONAL ACOUSTOELECTRONIC IMAGING AND CHARACTERIZATION OF OBJECTS

(75) Inventors: John D. G. Rather, Grosse Pointe, MI (US); H. John Caulfield, Cornersville, TN (US); Richard D. Doolittle, Bethesda, MD (US); Glenn W. Zeiders, Huntsville, AL (US); Gregory W. Auner, Livonia, MI (US)

(73) Assignee: Barbara Ann Karmanos Cancer Center, Detroit, MI (US)

( * ) Notice: Subject to any disclaimer, the term of this patent is extended or adjusted under 35 U.S.C. 154(b) by 32 days.

(21) Appl. No.: 10/082,656

(22) Filed: Feb. 25, 2002

(65) Prior Publication Data

US 2002/0138000 A1 Sep. 26, 2002

Related U.S. Application Data

(62) Division of application No. 09/650,306, filed on Aug. 29, 2000.

(51) Int. Cl.[7] .......................... G01N 29/06; G03H 3/00; A61B 8/15
(52) U.S. Cl. .......................... 73/603; 73/602; 600/448; 367/8
(58) Field of Search ...................... 73/602–605; 367/8; 600/448, 437

(56) References Cited

U.S. PATENT DOCUMENTS

| | | | | |
|---|---|---|---|---|
| 3,666,884 A | * | 5/1972 | Chambers et al. ............. 73/604 |
| 3,912,880 A | | 10/1975 | Powter et al. | |
| 3,942,150 A | * | 3/1976 | Booth et al. .................... 367/8 |
| 4,070,643 A | * | 1/1978 | Green ............................. 367/8 |
| 4,258,574 A | * | 3/1981 | Hildebrand et al. .......... 73/625 |
| 4,314,739 A | * | 2/1982 | Mehlum et al. ............... 359/9 |
| 4,415,996 A | * | 11/1983 | Maynard et al. ............... 367/8 |
| 4,507,966 A | * | 4/1985 | Crostack ...................... 73/603 |
| 4,531,410 A | * | 7/1985 | Crostack ...................... 73/603 |
| 5,031,154 A | * | 7/1991 | Watanabe ...................... 367/8 |
| 5,419,327 A | | 5/1995 | Rohwedder et al. | |
| 5,435,312 A | | 7/1995 | Spivey et al. | |
| 5,793,703 A | | 8/1998 | Shippey | |
| 6,027,448 A | | 2/2000 | Hossack et al. | |
| 6,171,246 B1 | | 1/2001 | Averkiou et al. | |
| 6,262,818 B1 | * | 7/2001 | Cuche et al. ................... 359/9 |
| 6,269,170 B1 | * | 7/2001 | Horikoshi et al. .......... 382/100 |
| 6,336,899 B1 | | 1/2002 | Yamazaki | |
| 6,385,474 B1 | * | 5/2002 | Rather et al. ............... 600/407 |

OTHER PUBLICATIONS

Lasser, et al., "Real–Time, Speckle Free Ultrasound Applications Using Novel Ultrasonic Camera System,".
Lasser, et al., "Real time, large area ultrasound imaging system using two–dimensional array technique," NDTnet, vol. 3, No. 3, Mar. 1998.
"About ADI," Advanced Diagnostics Incorporated Home Page, http://www.advdiag.com/.
"The World's First Ultrasonic Camera," Imperium, Inc., http//www.imperiuminc.com/product_info.htm.
Hildebrand et al., "An Introduction to Acoustical Holography," Plenum Press, New York 1972.
Rodney M. Powell, "Digital Holography," AFRL–M-N–EG–RT–2000–7045, Feb. 2000.

* cited by examiner

*Primary Examiner*—Hezron Williams
*Assistant Examiner*—John Hanley
(74) *Attorney, Agent, or Firm*—Townsend and Townsend and Crew LLP

(57) ABSTRACT

An acoustoelectronic method and apparatus for generating real-time three-dimensional images of an object and characterizing such object are provided. The object is insonified with an incident acoustic signal derived from an electrical signal. Acoustic signals scattered from the object are collected by an acoustic receiver, which generates analog electrical signals that are subsequently converted to digital electronic signals. The digital electronic signals are used in both direct-imaging and holographic methods to produce a three-dimensional representation of the object from which images and characterizations can be generated.

17 Claims, 6 Drawing Sheets

REAL-TIME THREE DIMENSIONAL ACOUSTOELECTRONIC IMAGING AND CHARACTERIZATION OF OBJECTS

CROSS REFERENCE TO RELATED APPLICATION

This application is a divisional application of and claims priority to U.S. Appl. Ser. No. 09/650,306, filed Aug. 29, 2000 the entire disclosure of which is herein incorporated by reference for all purposes.

BACKGROUND OF THE INVENTION

The present invention relates generally to a method and apparatus for imaging and analyzing objects using ultrasound. More specifically, the invention relates to a method and apparatus for real-time three-dimensional acoustoelectronic imaging, including both direct-imaging and acoustic holographic methods, to image and analyze tissue and tissue structures.

Because of certain disadvantages with other techniques, the medical community has looked to ultrasound to provide a safe, low-cost, high-resolution imaging tool. For example, imaging systems based on x-rays, including x-ray mammography and x-ray computed tomography (CT), are limited to providing images of pathologies within a body and do not characterize the features in an independently meaningful way. Techniques based on nuclear magnetic resonance, such as functional MRI, are more sophisticated and can provide physical characteristics of tissue, but they are slow and expensive, and therefore unsuitable for routine screening applications. Also, x-ray-based techniques use ionizing radiation, which is known to present certain health risks to patients. In addition to the relatively high expense associated with CT scans and MRI, the expertise of highly trained personnel is needed for extended periods of time to operate the devices and interpret the results. Perhaps most important, however, is the fact that these techniques rely exclusively on two-dimensional images, thereby disguising three-dimensional structure information that can be critical for diagnosis. Efforts have been made to produce pseudo-three-dimensional images (or 2.5-dimensional images) by collecting multiple discrete two-dimensional image slices, but these are not as valuable interpretively as a proper three-dimensional technique.

Acoustic waves propagate through inviscid liquids as longitudinal waves. Through viscous liquids and solids, acoustic waves may propagate as either longitudinal or shear waves and may be converted from one type to the other at boundaries between media of differing acoustic properties. The principal property determining the scattering of acoustic waves from these boundaries is the wave impedance $\rho c$, where $\rho$ is the density of the medium and $c$ is the sound speed, which generally has complex values in attenuating media. Since acoustic waves scatter at all boundaries and since the details of the scattering contain information about the two media in contact where the scattering arises, it is an objective of diagnostic ultrasound to recover the information available from the scattering. B- and C-scans are limited to backscatter in this regard. Transmission techniques use mostly the forward scatter. It is well known that different information is derived from the scatter depending upon the scattering angle with respect to the initial sound at which it is received. Thus, it is desirable to receive as much scattering information as possible.

In conventional B- and C-scan ultrasound analysis, a small array of approximately 1000 elements is moved by hand in contact with the patient. The array sends out acoustic waves that reflect from tissues back to the same array. Trained technicians and physicians conduct the ultrasound imaging procedure and interpret the results. The technique is well known to be limited in application because ultrasonic B and C scans provide only reflectivity information, which is most significant at boundaries between different types of materials, without providing other information on the properties of the materials themselves. In particular, the reflectivity is determined by the ratio of wave impedance, which involves the properties of both media forming the boundary. A change in reflectivity produces the strong reflections used in B-scans. Furthermore, the only radiation that is used is that reflected back to the hand-held sensing array. Depending on the ultrasound frequency, resolution is approximately 1–2 mm at a depth of 2–3 cm and about 5–7 mm at a depth of 5–6 cm.

There thus remains a need in medical imaging for a noninvasive method and apparatus that captures and analyzes full-field through-transmission data to provide full three-dimensional imaging and characterization of tissues.

SUMMARY OF THE INVENTION

Embodiments of the present invention provide an acoustoelectronic method and apparatus for generating a real-time three-dimensional representation of an object. Such embodiments improve on the two-dimensional ultrasound shadowgram images of the prior art. In one embodiment, the three-dimensional representation is generated by direct acoustoelectronic imaging. A first electrical signal is generated and used to derive an incident acoustic signal that insonifies the object. Resulting acoustic signals scattered from the object are collected and converted to digital electronic signals at substantially a rate defined by the frequency of the acoustic signal. The digital electronic signals are each time-resolved into an amplitude and phase from which the three-dimensional representation of the object is then produced.

In one such direct-imaging embodiment, additional information for producing the three-dimensional representation of the object is obtained by comparing the amplitude and phase of a reference electrical signal with the time-resolved amplitudes and phases of the digital electronic signals. The reference electrical signal may be derived from the same first electrical signal used to derive the incident acoustic signal. The first electrical signal may be a shaped electrical pulse or a continuous-wave electrical signal in different embodiments. In various embodiments, the scattered acoustic signals are collected at a two-dimensional array of acoustic receivers. Each acoustic signal received at the array is independently digitized, thereby permitting parallelization that allows hundreds of scans of the object to be completed within the standard $\frac{1}{30}$-s period used for video images.

Certain of the direct-imaging embodiments further include acoustic lenses. In one such embodiment, a transmitter acoustic lens is positioned so that the incident acoustic signal passes through the lens towards the object. Additional imaging information is acquired by also positioning a second transmitter acoustic lens through which an orthogonally directed incident acoustic signal passes towards the object. Such transmitter lenses may be moveable along the respective propagation directions to focus the acoustic signals at particular locations within the object. In a certain embodiment, a receiver acoustic lens is positioned to focus the scattered acoustic signals onto the acoustic receiver.

In further direct-imaging embodiments, the acoustic transmitter is a pixelated two-dimensional transducer array, which is suitable for near-field focal region scanning of the object. Scanning is achieved in one such embodiment by varying the frequency of the incident acoustic signal as emitted from different pixels of the transducer array. In an alternative embodiment, the amplitude of the incident acoustic signal is varied for different pixels. In a particular embodiment, the transducer array is circular with independently driven radial ring separations and is configured successively to excite increasing numbers of such radial rings. In a related embodiment, the circular transducer array is sectioned radially and circumferentially and configured to quadratically vary the phase of the incident acoustic signal emitted from different pixels.

Other embodiments of the invention are directed to generating a real-time holographic representation of the object. A first electrical signal is generated and used to derive an incident acoustic signal to insonify the object. Scattered acoustic signals are then collected from the insonified object and converted to digital electronic signals for recording an electronic interference pattern. The representation of the object is obtained from the recorded pattern from a computational reconstruction of the wavefront by electronically diffracting a reference electrical signal with the recorded pattern. The reference electrical signal may be generated from the first electrical signal, which is a shaped electrical pulse or a continuous-wave electrical signal in different embodiments. The scattered acoustic signals are collected in one embodiment at a two-dimensional array of acoustic receivers. In further embodiments, multiple acoustic sources and multiple two-dimensional acoustic receiver arrays are used.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components.

DESCRIPTION OF THE SPECIFIC EMBODIMENTS

I. Acoustic Holography

Figure 1:
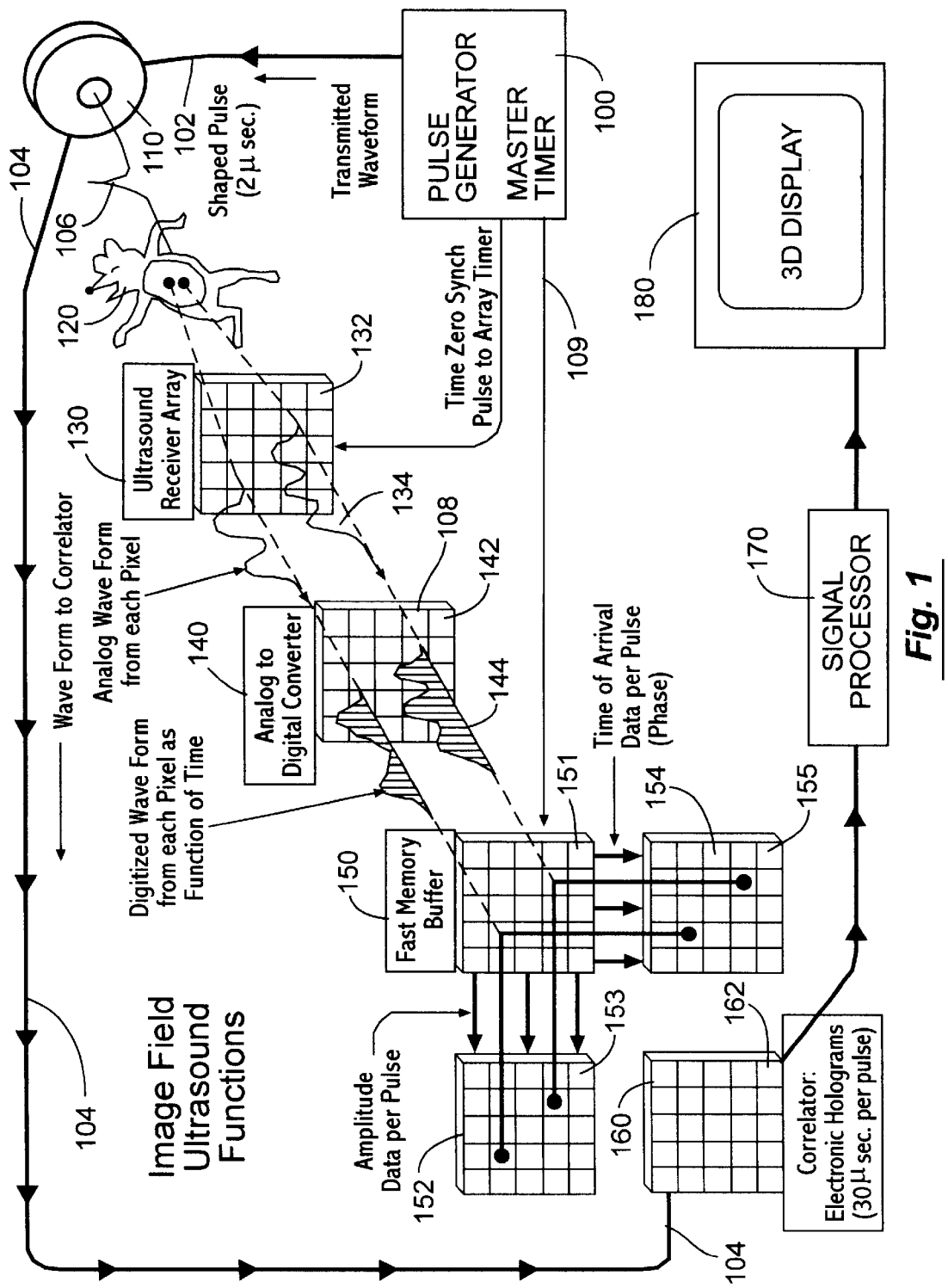
FIG. 1 is a schematic overview of the electronic image-field ultrasound acoustic holographic technique of the invention.

Holography, invented by Dennis Gabor in 1948, is a technique that combines principles of interferometry (for recording a hologram) and diffraction (for displaying the image). Most simply, a coherent beam of radiation is scattered by an object and the interference pattern created between the scattered beam and a reference beam is recorded. In optics, the reference beam is a portion of the original coherent beam that has been reflected to bypass the scattering object. The recorded interference pattern preserves a complete record of both the amplitude and phase distributions of the scattered beam. For example, with electromagnetic-based holography, the interference pattern may be stored on photographic film. Even though the film itself responds only to light intensity, amplitude information is preserved as a modulation of the depth of interference fringes and phase information is preserved as variations of the position of the fringes.

When a coherent beam is subsequently diffracted from the recorded interference pattern, the original scattered beam can be recovered. Thus, in the electromagnetic example, when a photographic transparency of the interference pattern is illuminated with coherent light, a transmitted wave component is an exact duplication of the original object beam and accordingly generates a virtual image of the object. This image is truly three-dimensional because all spatial information of the scattered beam is recovered from the diffraction.

While electromagnetic holography is more familiar, the same principles apply when the coherent beam is acoustic. The interference between a reference acoustic signal and a scattered acoustic signal generates sufficient amplitude and phase information to produce a visual image of an object irradiated with invisible energy. One obstacle in the development of acoustic holographic techniques has been the lack of a convenient recording medium since photographic film is not normally sensitive to sound and there are no immediate acoustic analogues. The two main methods of investigation have thus been the use of liquid-gas interfaces or the use of point-by-point sampling methods.

In a liquid-gas interface technique using water and air, for example, two underwater transducer sound sources are used to generate the reference beam and to scatter off the object to produce the scattered beam. The beams produce an interference pattern at the surface of the water, causing it to have minute stationary ripples. These mechanical deformations of the liquid surface correspond exactly to the interference fringes of a hologram so that an immediate visual construction of the hologram is accomplished by diffracting laser light off the pattern. In a sampling method, the physical limitation imposed by the fact that an acoustic receiver cannot be made infinitely small is addressed. The sampling theorem states that any wavefront extending over any aperture A, containing spatial variations limited to a line density B, is completely specified by sampling at intervals of ½B.

One commercially available ultrasound imaging device is the Acoustocam I100 camera made by Imperium, Inc. of Rockville, Md. This device also produces a two-dimensional shadowgram at the focus of its lenses. It operates by pulsing a large-area unfocused ultrasound transducer to generate a plane acoustic wave that strikes the target. An acoustic lens collects the scattered wave and focuses it onto a receiver array made of a piezoelectric material that is deposited directly onto a silicon readout multiplexer. The piezoelectric response to the incident acoustic wave produces voltages read by the multiplexer. Standard real-time image processing techniques are used to format this voltage response into an image for presentation. By adjusting the focus of the lens, planar shadowgrams at different depths in the target are produced. Since the receiver array does not time-resolve the ultrasound wave amplitude and phase, it merely integrates the total energy formed upon each pixel for the duration of a video frame (e.g., 1/30 second).

A commercially available product that uses acoustic holographic imaging is the ultrasound holographic system from ADI, Inc. in Richland, Wash. This device uses a visible laser for wavefront reconstruction from recorded acoustical data. Because such a visible laser has a wavelength ~1/1000 of a typical ultrasound-signal wavelength, however, a large amount of longitudinal demagnification occurs during reconstruction. Acoustic lenses help prevent lateral demagnification, but the holographically reconstructed image has essentially negligible depth of field, producing essentially a two-dimensional shadowgram image similar to an x-ray.

This general limitation imposed by the large difference in acoustic and visible electromagnetic wavelengths has hampered previous acoustic holographic approaches. It has long been known that a wavefront specified on some surface can be theoretically propagated both forwards and backwards by using the well-known wave equation. Acoustic holographic approaches have attempted to view reconstruction of the wavefront at a visible wavelength $\lambda_V$ even though the hologram was formed at a sound wavelength $\lambda_S$. This produces a demagnification of images formed by propagation from the hologram proportional to $\lambda_S/\lambda_V$ (~1000). By imaging the object onto the hologram plane, acoustic holography has provided some information, but its depth resolution is equivalent to ordinary imaging.

According to one embodiment of the present invention, a full three-dimensional image is obtained as in visible-light holography. This is done without distortion by requiring the ratio $\lambda_S/\lambda_V$ to be substantially equal to 1. This is achieved by recording a hologram using an acoustic wavelength $\lambda_S$ and performing the wavefront reconstruction and wavefront propagation computationally with the identical wavelength. Since the reconstructing wavelength is just a parameter setting in a computer program, no wavelength is any more difficult than any other.

Various embodiments of the invention as described below include both holographic and direct imaging techniques that make use of acoustoelectronic reconstruction. In certain embodiments, reflected sound waves are recovered as well as transmitted sound waves, in either direct imaging or holography. This is useful, for example, in imaging the human breast because cancers often tend to form near the chest wall in regions that are difficult to image by conventional transmissive acoustic imaging. Such reflected sound waves may be examined off-axis from the insonifying beam or may use a beam splitter for on-axis viewing.

II. Electronic Image-Field Ultrasound Waveform Analysis and Acoustic Holography

Sound waves travel through the entire thickness of the human body in about 0.05 ms. This relatively slow rate permits the use of micro-electromechanical systems (MEMS) and similar devices to acquire and process the acoustic data in real time. This propagation time also sets a limit on the rate at which information can be gathered to form a diagnostic data set, particularly in cases where the data acquisition method requires sequential measurements of propagation from every (Nyquist-determined) transmission point to every receiving point. This limit is addressed in embodiments of the present invention by using parallelism in data acquisition and processing.

FIG. 1 presents a generic representation of a system and method for acoustoelectronic imaging in accordance with embodiments of the present invention. By electronically digitizing scattered acoustic data as explained below and using an electronic reference signal, improvements in generating a three-dimensional image are realized. Although the different functional levels are shown schematically in the figure as separate array slabs, they are preferably integrated together on a microchip.

A master timer 100 triggers an electrical-signal generator that propagates an electrical pulse or continuous-wave (CW) electrical signal along path 102 to ultrasound source 110. In one embodiment where the object under study 120 is tissue, the electrical-signal generator produces a series of pulses 106 with a typical pulse repetition frequency (PRF) of about 30 kHz, which is appropriate for the propagation time of the resulting acoustic signals through the tissue. The electrical pulse energizes the ultrasound source 110, which preferably comprises a piezoelectric material (such as Pb—Zr—Ti oxides, i.e. PZT) that responds to such a pulse. The ultrasound source 110 transmits a plurality of shaped pulses 106 towards the object under study 120, the pulses 106 having a wave envelope designed to optimize data interpretability. In a particular embodiment where the object under study is tissue, the pulses 106 are typically about 2-$\mu$s broadband bursts of about ten oscillations with a center frequency of approximately 5 MHz and having frequency components extending between approximately 1 to 10 MHz.

In some embodiments, this pulse profile is also routed along path 104 directly to the detection correlator 160, where it is used to generate a reference signal in the data interpretation process. In particular, in one embodiment, the pulse profile triggers a two-dimensional perfect wave synthesis in the digitized data field to serve as the reference signal. In an alternative embodiment, the pulse profile excites an analog reference in a physical layer of the ultrasound receiver array 130 matrix before digitization. The ultrasound pulses 106 propagate through the object under study 120 and impinge an ultrasound receiver array 130. At 30 kHz PRF, for example, six pulses will be proceeding in sequence along a 300-mm diameter path at any given instant. This pulse separation (33 $\mu$s) permits approximately 1000 frames of data to be gathered in the 33 ms time required for one frame of a standard video monitor display (typically 1/30 s). In all the embodiments discussed, the object under study 120 is surrounded by an impedance-matching medium such as water or gel to ensure adequate transmission of the acoustic waves into the object.

The receiver array 130 is preferably comprised of a number of receiver elements 132 ("receiver pixels") arranged as a two-dimensional array. Each receiver pixel is an ultrasonic transducer that responds to the impinging waves scattered by the object under study 120 by generating an analog signal 134 corresponding the received wavetrain. For each receiver pixel 132, the analog signal 134 is then captured and processed such that the underlying three-dimensional distribution of information pertaining to every resolvable element of the object under study 120 is derived as a function of time, essentially at the ultrasound wave frequencies. In a preferred embodiment, this is achieved by using A/D pixels 142 of an analog-to-digital converter 140 to convert the analog ultrasound signals 134 to digitized signals 144. The collection of digitized data is then transferred to a fast memory buffer 150 that parses the data for each buffer pixel 151 into components for further processing.

In one embodiment, for example, the amplitude 152 and phase components 154 of the digitized waveforms are extracted from the fast memory buffer 150 in separate arrays of amplitude pixels 153 and phase pixels 155. The signal amplitudes are derived from the strength of the signals and the phases are determined through comparisons with synchronization signals 108 and 109 delivered from the master timer 100 to the analog-to-digital converter 140 and fast memory buffer 150 respectively. This amplitude and phase data extracted from the fast memory buffer 150 are used by a correlator 160 to produce a visual image representation of the object under study 120.

The correlator 160 exploits the fact that the extracted amplitude and phase pattern constitutes a description of a wavefront. Given the wavelength and sound speed, these data are used to propagate the wavefront into object space computationally. At any surface within a reconstructed wavefront corresponding to the object, the amplitude of that back-propagated wavefront provides a representation of the shape of the object. Similar computations for multiple depths within the object collectively provide an ensemble of tomographic images, which serve as a three-dimensional object description. This object description may in turn be used to produce the visual image representation of the object under study 120.

Figure 2:
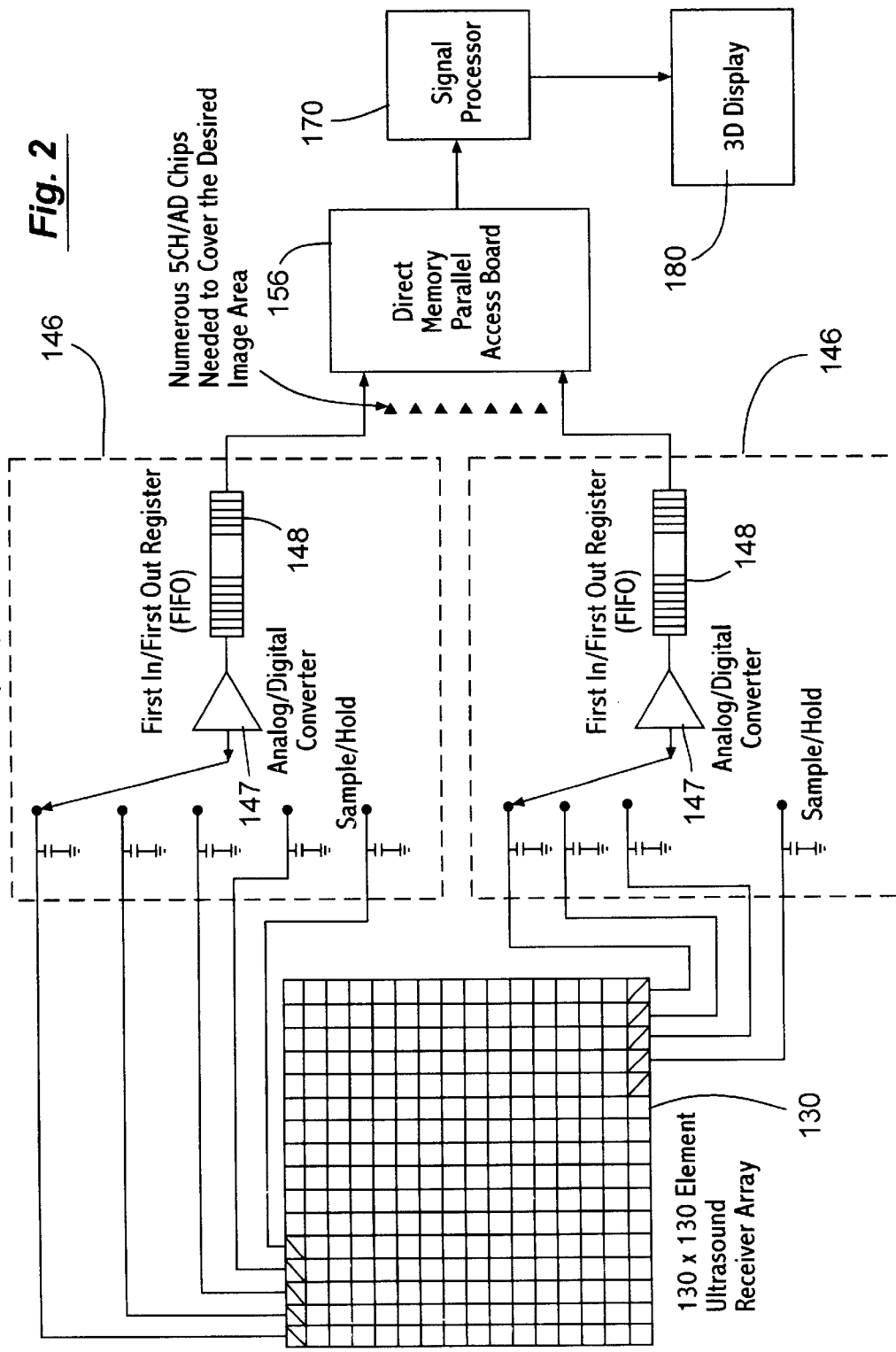
FIG. 2 illustrates one embodiment of the image-field array chip and processor board structure in accordance with the invention.

One embodiment of the image-field array of the present invention is shown in FIG. 2, where it is illustrated as a processor chip for a 130×130 element receiver array 130, although the invention is not limited to any particular array density. Each of several multichannel processors 146 (five-channel processors in the illustrated embodiment), including analog-to-digital converters 147 and memory register chips 148, is used to collect and digitize the scattered acoustic radiation. Sufficiently many multichannel processors 146 are used to cover all pixels 132 in the receiver array 130. In the illustrated embodiment, the memory register chips 148 are first-in-first-out chips to capture the digitized information, which is subsequently fed to a direct memory parallel access board 156 and then to the signal processor 170. With this configuration, the image-field array processor chip permits significant parallelization in the capture and processing of the full ultrasonic wavetrain acting on each pixel for real-time construction of images and postprocessing analysis of wave components. The detailed digital characterization of pulse shape, time of flight, and amplitude of the data contains sufficient information for imaging and tissue characterization.

In another embodiment, an electronic reference signal from which the initial shaped pulse was generated is propagated along path 104 to the correlator 160. On a pixel-by-pixel 162 basis, the correlator 160 constructs an overlap of the digitized waves scattered from the object under study 120 with the electronic reference signal to construct a holographic representation of the object under study 120 electronically at a rate of approximately 30 $\mu$s/image. Standard holographic analysis techniques may be used in this construction. This holographic representation is then processed using standard techniques with a signal processor 170 for display of a visual image of the object under study 120 on a display device 180. The resulting images improve over the prior two-dimensional shadowgrams by providing the full depth of the image field in real time. They also include the full physical information required to enable accurate characterization of the physical scattering properties of every resolvable volume element in the three-dimensional volume occupied by the object under study 120.

III. Near-Field Focal-Region Scanner for Tissue Diagnostics

Figure 3:
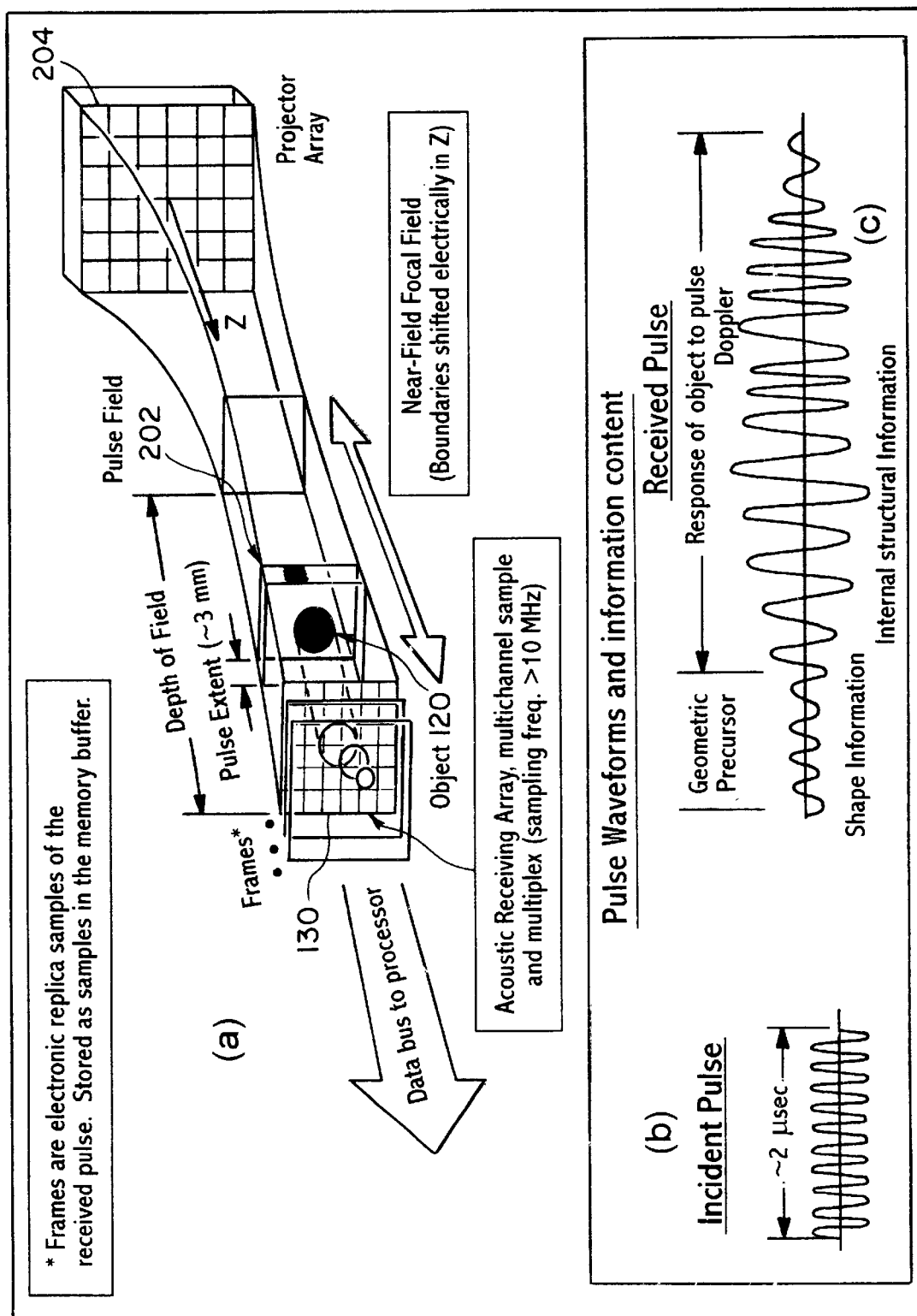
FIG. 3 is a schematic illustration of a near-field focal-region scanner embodiment of the invention: part (a) shows the general structure of the near-field scanner; part (b) shows the pulse incident on the object under study; and part (c) shows the pulse received by the receiver array.

In still a further embodiment, illustrated in FIG. 3, the invention is directed to a near-field focal-region scanner for application in tissue diagnostics. The scanner relies on the particular use of the near-field (with respect to the object under study) for insonifying the object under study, which is then characterized through analysis of its response in the forward direction to an ultrasound pulse. As shown in FIG. 3($a$), the incident pulse form 202 has a continuous-wave (CW) envelope with fixed power and frequency, although alternatively individual pulses encoded to allow time resolution are also within the scope of the invention.

A sectioned transducer 204 transmits the pulse, which follows a physical envelope defined by the shape and electronic phasing of the transducer 204. In the illustrated embodiment, the transducer 204 is square and the envelope is defined by projection of the corners of the square along the propagation axis. Other transducer shapes are possible, leading to different shapes of the pulse beam. The "near-field" focal region is analogous to the confocal region surrounding a beam waist in electromagnetic optics. It refers to the broad maximum in the pressure that extends from the Fresnel zone to the far zone. In the Fresnel zone, a plane normal to the propagation axis has a phase distribution with a pattern that scales in range, becoming more compressed towards the central axis as the range increases. The axial pressure in the Fresnel region has zero pressure points separated along the propagation axis until the beginning of the broad maximum is reached. At distances beyond this point, the near-field beam reaches its maximum compression, being roughly cylindrical in shape, and then falls off as a quasi plane wave.

For a fully baffled circular transducer of radius a, the maximum pressure along the propagation axis is at a distance $a^2/\lambda$. Thus for an acoustic frequency of 5 MHz, a 1-mm transducer radius provides a range of 3.3 mm; a 10-mm transducer radius provides a range of 300 mm. The extent of the range also varies with radius. For $\alpha=10$ mm, the extent is approximately 60–200 mm. If the transducer has some curvature, e.g. negative on the transmitting side such as for a spherical segment radiating inwards, it shortens and intensifies this region. Methods for moving the position of this region along the propagation direction include adjusting the transducer frequency or, preferably, varying the amplitude distribution of the driving velocity radially to change the effective area of the transducer. Amplitude shading is possible with a sectioned transducer.

In one embodiment, a circular transducer is configured with independently driven radial ring separations. This permits successive scans to be made with an increasing number of rings being excited, thereby effecting scanning along the propagation axis. Other programs for applying radial distributions to the segmented transducer are also within the scope of the invention. For the preferred parameters cited above, there is sufficient time to complete hundreds of multiple scans without exceeding the $\frac{1}{30}$-s video rate. Scanning of the inner Fresnel zone lengthens the effective focal region. In another embodiment where the circular transducer is sectioned circumferentially as well as radially, quadratic phasing is implemented to steer the near-field region off axis. Thus, in this embodiment, the device includes a raster scanning capability and permits increased volumetric coverage with each transducer.

Interaction of the pulse 202 with the object under study 120 not only diffracts the pulse 202 around the object and transmits a portion of the pulse 202 through the object, but excites the object into motion, thereby radiating an additional acoustic signal characteristic of its acoustic properties. This re-radiation resulting from the induced motion of the object under study 120 creates an acoustic wake that follows the pulse received at the receiver array 130. As described above, the pixelated receiver array 130 converts the acoustic pressure to an electrical signal for each pixel and a local multichannel analog-to-digital converter samples each waveform and multiplexes the converted digital time series sequence.

In FIGS. 3(b) and 3(c) are shown schematic representations of the incident and received waveforms. The incident pulse in FIG. 3(b) is the preferred 2-μs broadband burst of ten oscillations with a center frequency of approximately 5 MHz. The corresponding pulse received after interacting with the object under study 120, shown in FIG. 3(c), has two distinct regions. The first portion of the pulse, identified by the label "geometric precursor" in the figure, contains shape information that is used to generate an electronic interferogram for producing the holographic image in an embodiment. The second portion of the pulse contains additional internal structural information resulting from induced vibration of the object under study. In addition, one feature shown is an increase and decrease of oscillation frequency 120, identified in the figure by the label "Doppler," which results from motion within the object (e.g. such as blood motion within tissue) causing a Doppler shift. This information may be analyzed using any known time-domain or frequency-domain data processing technique.

IV. Lens-Based Electronic Image-Field Acoustic Imaging

Figure 4:
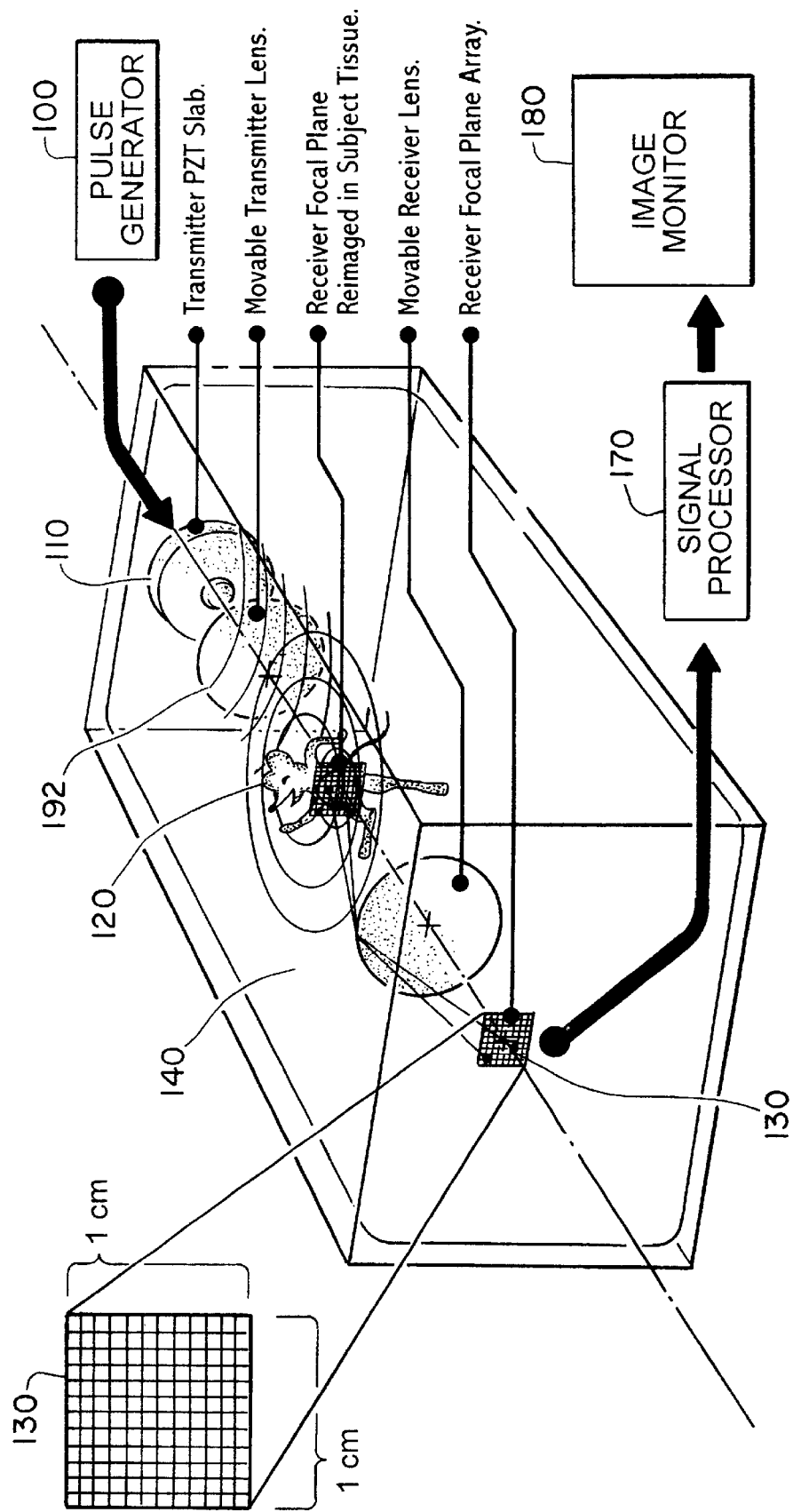
FIG. 4 is a schematic illustration of an acoustic-lens-based direct-imaging embodiment of the image-field ultrasound acoustic method and apparatus.

One direct-imaging embodiment of the invention that comprises ultrasonic lensing techniques for reimaging a slab of an insonified object onto the detecting array is shown in FIG. 4. In this embodiment, path inhomogeneities beyond the depth of focus (i.e. beyond a few sonic wavelengths) are not sharply focused, and therefore produce only slight smearing without further interference. In this embodiment, the acoustic system is lens-based, including ultrasonic receiver lens 190 mounted on a moving stage (not shown). Receiver lens 190 is used to focus the acoustic waves onto the receiver array 130. FIG. 4 also shows transmitter lens 192, which is used in a confocal embodiment described below, but is unneeded for other embodiments of the invention. Although not shown explicitly in FIG. 4, the electronic elements described with reference to FIG. 1 are used for the electronic construction in the manner previously described.

By moving the stage that holds the ultrasonic receiver lens 190 in incremental fashion, an acoustic snapshot is recorded for each depth of focus through the object under study 120, thereby fully capturing the volume of interest. For example, if the object under study 120 is 30 cm deep and the lens system has a 1-mm depth of field, the volume of interest can be captured with 300 acoustic snapshots over a 30 ms time period. In another embodiment, two arrangements such as shown in FIG. 4 are used in a substantially orthogonal orientation, permitting extraction of information used to construct a full three-dimensional image. Other orientations are greater numbers of arrangements may also be used. When two (or more) sound beams are present simultaneously, interference will occur within the object under study 120. In certain embodiments, the beams are interrupted so that they are not present in the object at the same time and/or the beams are configured to insonify the object under study 120 with different frequencies.

As for conventional optics, the imaging system can be characterized by the numerical aperture $N_A$, which is a ratio of the focal length to lens diameter. The resulting object lateral resolution at wavelength $\lambda$ is about $\lambda N_A$ while the longitudinal resolution is $2\lambda N_A^2$. The numerical aperture cannot be made arbitrarily small, at least with material lenses, because of fabrication difficulties and reduced lateral field of view. The minimum resolution is thus approximately one wavelength. Using a configuration such as used by the Imperium camera, for example, with an aperture diameter of 5 cm and a numerical aperture of 1.0, the focus would be at 5 cm. For a 5 MHz acoustic wave ($\lambda$=0.3 mm), this would give a lateral resolution of 0.3 mm and a longitudinal resolution of 0.6 mm. A 10-cm lens with $N_A$=1.0 would similarly focus at 10 cm with the same resolution, but has twice the penetrating range.

Acoustic wave propagation through tissue is not ideal, and resolution can sometimes be significantly degraded by sound speed variations in the region between the object and the image. Variations in wave number $k \equiv 2\pi/\lambda$, where $\lambda$ is the acoustic wavelength in the tissue, can affect the phase, given by $\Delta\phi = \int (kx) dx$. The phase variation over arrivals of signals at the focus can exceed $2\pi$, with a corresponding shift in acoustic path length of many waves ($\lambda$=0.3 mm at 5 MHz). The use of small numerical apertures (i.e. small cone angles) can thus be beneficial in allowing the bulk of the signal to be unaffected by localized disturbances.

The balance between ideal diffraction, the phase degradation from sound speed variations, and the energy loss from absorption cause there to be an optimum operating frequency that depends on both the ultrasonic equipment and the subject. The detectors and transmitters of known medical ultrasonic devices are typically tuned to a frequency of 5 MHz, but the invention is not limited to any particular operation frequency. The physical arrangement used by the invention has sufficient variation in numerical aperture and range of motion for receiver lens 190 to accommodate broadband operating capability.

In another embodiment, moveable transmitter lens 192 is included in the acoustic system as shown in FIG. 4. The effect of the transmitter lens is to minimize degradation of the resolution of the received signal that results from inhomogeneities on the recording surface by using a confocal imaging technique. In acoustic confocal imaging, the sound source is focused within the object under study 120 by the transmitter lens 192, thus restricting the field of view to a well-defined focused spot. The spot is imaged using the electronic image-field acoustic technique described above. Because the field of view is restricted in confocal imaging, scanning throughout the object under study in the desired three dimensions is needed to obtain a complete image. In the illustrated embodiment, such scanning is achieved by incremental stage motion of the transmitter lens 192 and possibly also the receiver lens 190.

V. Electronic Image-Field Acoustic Holography

Figure 5:
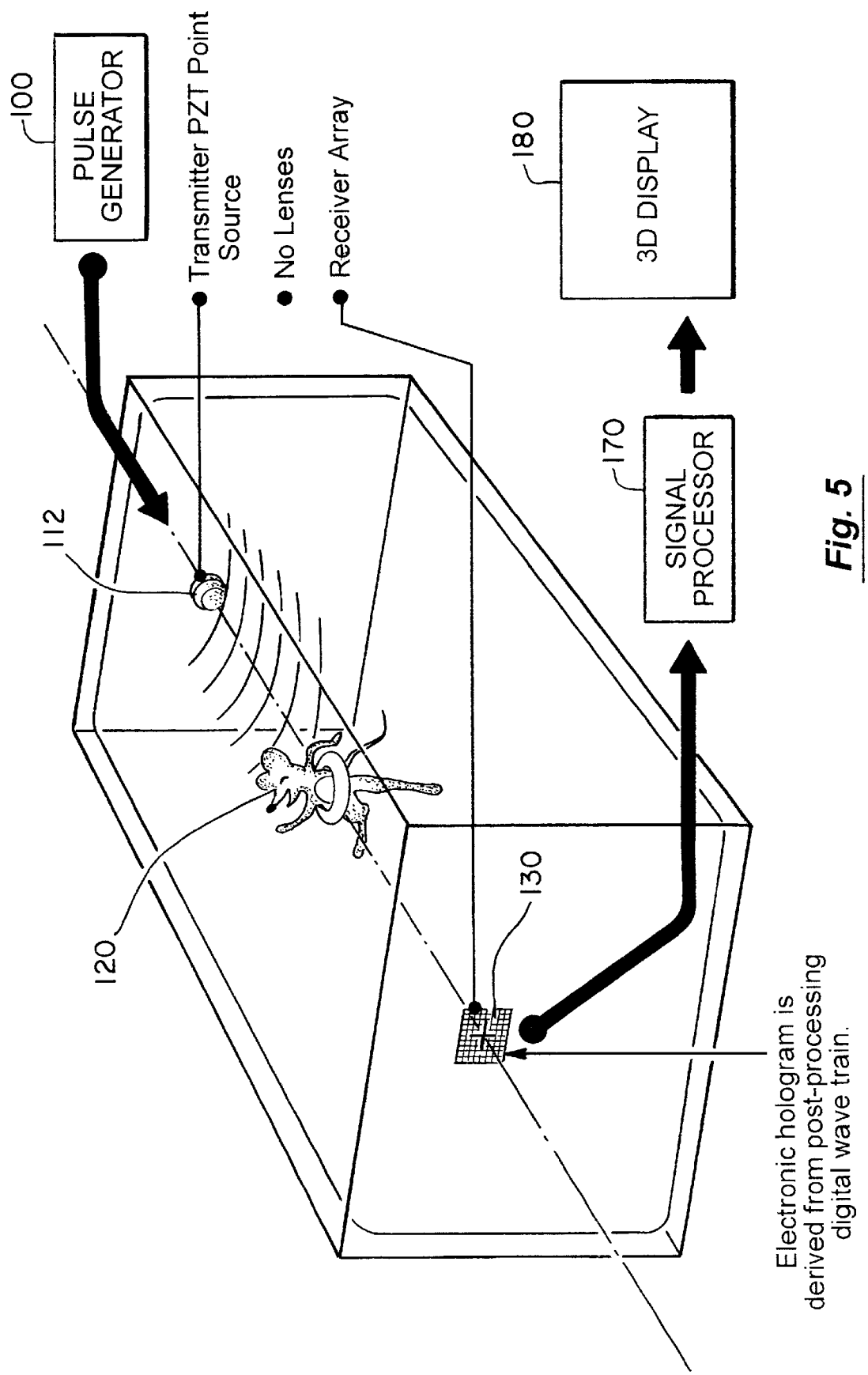
FIG. 5 is a schematic illustration of a lensless holographic embodiment of the image-field ultrasound acoustic holographic method and apparatus.

A lensless embodiment of the invention that uses holographic image construction is shown in FIG. 5. The overall configuration is similar to the lens-based embodiment illustrated in FIG. 4. Lensless acoustic holography is accomplished by using an array of fast detectors to record directly the wavefront detected by each pixel of the receiving array 130 at three or four times per wave cycle, and by electronically reconstructing the hologram rather than by using coherent laser light as in previous art. For each pixel, a raw signal of the form $$\psi_1 = A_1 e^{i(\omega t + \phi_1)},$$

where A, ω, and φ are used generally to denote the amplitude, angular frequency, and phase defining a wave signal ψ, is received after scattering off the object of interest 120. This is mixed with a mutually coherent reference signal of the form $$\psi_2 = A_2 e^{i(\omega t + \phi_2)}$$

to produce the mixed signal $$\psi = \psi_1 + \psi_2 = (A_1 e^{i\phi_1} + A_2 e^{i\phi_2}) e^{i\omega t}.$$

As noted previously, the reference signal may be obtained from the original pulse, a component of which is scattered off the object under study. Application of the raw signal or reference signal alone gives a wave with intensity $A_1^2$ or $A_2^2$ respectively, while the phase-difference information between the raw and reference signals is preserved in the intensity of the mixed signal, $$|\psi|^2 = |\psi_1 + \psi_2|^2 = A_1^2 + A_2^2 + 2A_1A_2 \cos(\phi_1 - \phi_2).$$

Since the time dependence drops out of the intensity of the mixed signal, fully electronic injection of the reference signal $\psi_2$ with the recorded raw signal $\psi_1$ enables amplitude and phase information to be extracted computationally for lensless operation without requiring time-resolved measurements.

Stated differently, the on-chip electronics algebraically adds the 5 MHz waves to either a real reference wave or a virtual wave reference field, thus creating a hologram at the ultrasound frequency. Further processing built into the chip then performs transforms as necessary to recover the image field in a cross section through the sampled volume. Introduction of a series of phase delays to the reference wave effectively moves the sampled plane through the volume in parallel, thereby recovering information throughout the space. In this embodiment, the hologram is produced only once for a given time series of pulses, thus freezing the data field until the post-processing reads out the entire volume. Phase and amplitude information are thus recovered for all volume elements of the object under study, and the output data stream is transmitted at video rates for image formation.

VI. Multiple Acoustoelectronic Imaging

Figure 6:
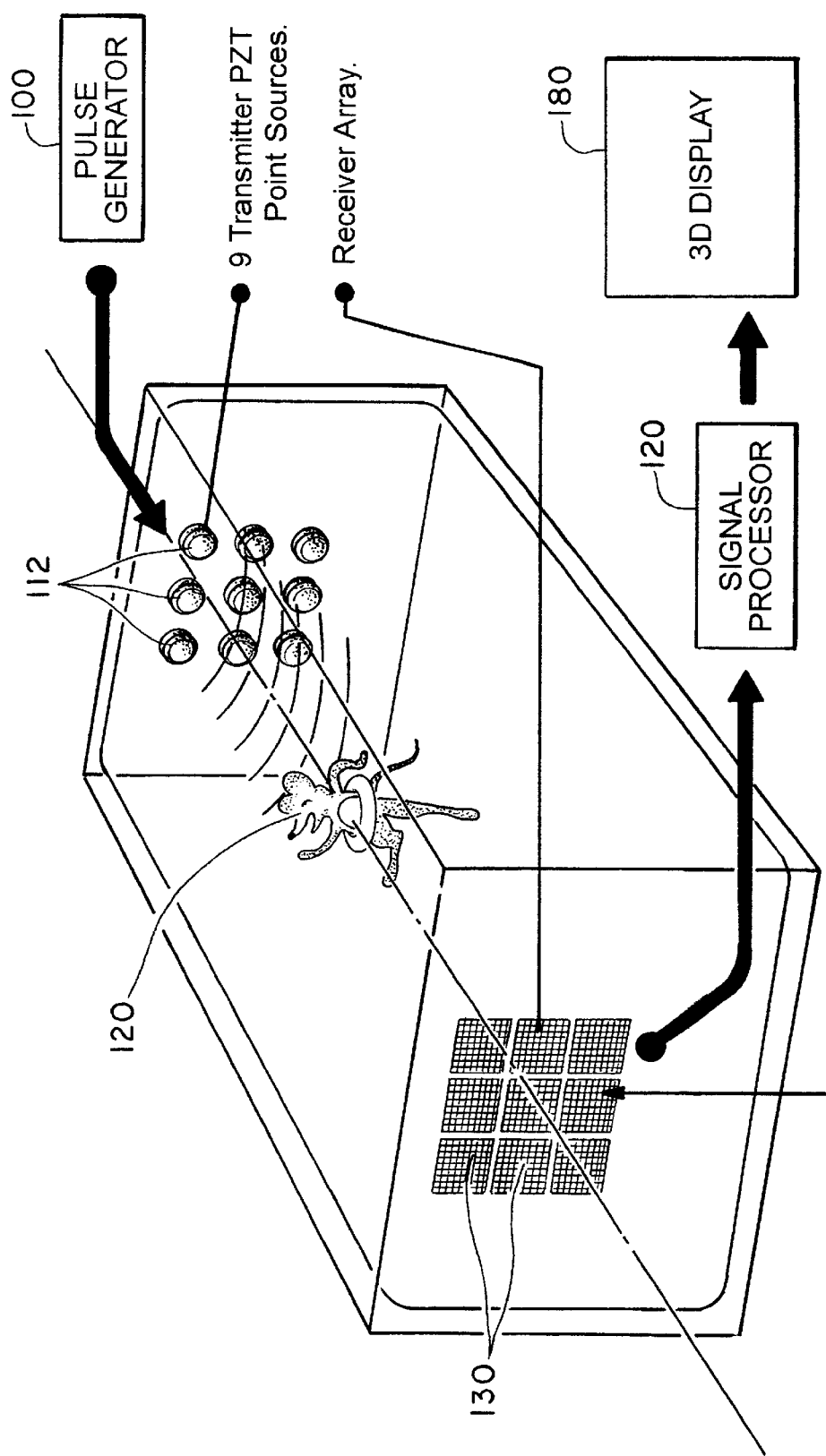
FIG. 6 is a schematic illustration of a multihologram embodiment of the invention.

FIG. 6 illustrates a further embodiment of the present invention in which multiple acoustic sources 112 and a superarray 135 comprised of multiple receiving arrays 130 are used (nine of each are shown in the figure, although very many more, e.g., as many as thousands, are also within the scope of the invention). In this embodiment, each individual receiving array 130 is used to derive an image, either directly or holographically, according to the particular embodiment of the invention. Because sound attenuates with passage through material, insonification from different positions produces different images. By recording multiple images, directly or holographically, better information regarding the structure of the object under study 120 is obtained. The multiple images are preferably recorded simultaneously to ensure that the object under study 120 has not moved or changed shape between individual recordings.

Various additional advantages ensue from the use of a multiple-source-multiple-receiver configuration, particularly in deriving correlations with tissue-type discriminants that can be used for automatic diagnosis of tissue pathologies. In one embodiment, many identical holographic chips are arranged together to conform to the overall shape of the human body, or a portion of the human body, thus providing large-volume sensing. Automatic pathology diagnosis may be achieved by training an appropriate pattern-recognition algorithm, such as a neural network, to recognize such characteristic discriminants. The general application of appropriate discriminants and pattern-recognition algorithms are described in detail in PCT application WO 99/47046 entitled "METHOD AND APPARATUS FOR HIGH-RESOLUTION DETECTION AND CHARACTERIZATION OF MEDICAL PATHOLOGIES," which is incorporated herein by reference for all purposes.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method for generating a real-time holographic representation of an object, the method comprising:
   (a) generating a first electrical signal;
   (b) insonifying the object with an incident acoustic signal derived from the first electrical signal;
   (c) collecting acoustic signals scattered from the insonified object;
   (d) converting the collected acoustic signals to digital electronic signals
   (e) converting the first electrical signal to a digital electronic signal;
   (f) generating an electronic interference pattern of the digitized first electrical signal and the digitized collected acoustic signals; and
   (g) computationally reconstructing a wavefront by electronically diffracting a reference signal with the generated electronic interference pattern.

2. The method according to claim 1 wherein the reference signal is generated from the first electrical signal.

3. The method according to claim 2 wherein the first electrical signal is a shaped electrical pulse.

4. The method according to claim 2 wherein the first electrical signal is a continuous-wave electrical signal.

5. The method according to claim 1 wherein the step of collecting acoustic signals scattered from the insonified object comprises receiving the scattered signals at a two-dimensional array of acoustic receivers.

6. The method according to claim 5 wherein the step of converting the scattered acoustic signals to digital electronic signals comprises independently digitizing a signal associated with each acoustic receiver in the two-dimensional array.

7. The method according to claim 1 wherein the step of insonifying the object with an incident acoustic signal derived from the first electrical signal comprises insonifying the object with a plurality of incident acoustic signals separately derived from the first electrical signal and the step of collecting acoustic signals scattered from the insonified object comprises receiving the scattered signals at a plurality of two-dimensional arrays of acoustic receivers.

8. The method according to claim 1 wherein the object is biological tissue and the first electrical signal is a broadband oscillation burst with a center frequency of approximately 5 MHz.

9. An apparatus for generating a real-time holographic representation of an object, the apparatus comprising:
   (a) an electrical signal generator configured to generate a first electrical signal;
   (b) an acoustic transmitter electrically connected to the electrical signal generator and configured to emit an incident acoustic signal derived from the first electrical signal for insonifying the object;
   (c) an acoustic receiver array positioned and configured to generate analog electrical signals in response to acoustic signals scattered from the insonified object;
   (d) an analog-to-digital converter electrically connected to the acoustic receiver and configured to convert the analog electrical signals to digital electronic signals;
   (e) a correlator electrically connected to the electrical signal generator and the analog-to-digital converter, and configured to convert the first electrical signal to a digital electronic signal and to generate an electronic interference pattern of the digitized first electrical signal and the digitized acoustic signals; and (f) a signal processor in electrical communication with the correlator and configured to computationally reconstruct a wavefront by electronically diffracting a reference signal with the generated electronic interference pattern.

10. The apparatus according to claim 9 wherein the reference signal is generated from the first electrical signal.

11. The apparatus according to claim 10 wherein the first electrical signal is a shaped electrical pulse.

12. The apparatus according to claim 10 wherein the first electrical signal is a continuous-wave electrical signal.

13. The apparatus according to claim 9 wherein the acoustic receiver comprises a two-dimensional array of material elements, each of which is capable of producing an analog electrical signal in response to an acoustic wave.

14. The apparatus according to claim 13 wherein the analog-to-digital converter is configured to convert each analog electrical signal generated from each such material element to a digital signal independently.

15. The apparatus according to claim 9 wherein the acoustic transmitter comprises a plurality of independently activated acoustic-transmitter elements and the acoustic receiver comprises a plurality of two-dimensional arrays of material elements, each capable of producing an analog electrical signal in response to an acoustic wave.

16. The apparatus according to claim 9 wherein the object is biological tissue and the first electrical signal is a broadband oscillation burst with a center frequency of approximately 5 MHz.

17. The apparatus according to claim 9 wherein the acoustic receiver array is electrically connected to the electrical signal generator and configured to convert the first electrical signal to an analog electronic signal in a physical layer of the acoustic receiver array.

* * * * *